(12) United States Patent
Hart, Jr. et al.

(10) Patent No.: US 9,347,851 B2
(45) Date of Patent: May 24, 2016

(54) SIGNAL PROCESSING OF LAMB WAVE DATA FOR PIPE INSPECTION

(71) Applicant: Lisa M. Leonard, Southbury, CT (US)

(72) Inventors: Glenn G. Hart, Jr., Suffield, CT (US);
Mark W. Kirby, Vernon, CT (US);
David S. Leonard, Southbury, CT (US);
John P. Lareau, Granby, CT (US)

(73) Assignee: Westinghouse Electric Company LLC, Cranberry Township, PA (US)

( * ) Notice: Subject to any disclaimer, the term of this patent is extended or adjusted under 35 U.S.C. 154(b) by 381 days.

(21) Appl. No.: 13/713,364

(22) Filed: Dec. 13, 2012

(65) Prior Publication Data
US 2013/0180337 A1 Jul. 18, 2013

Related U.S. Application Data

(60) Provisional application No. 61/570,472, filed on Dec. 14, 2011.

(51) Int. Cl.
| | |
|---|---|
| *G01N 29/04* | (2006.01) |
| *G01M 7/00* | (2006.01) |
| *G01N 29/12* | (2006.01) |
| *G01N 29/46* | (2006.01) |
| *G01N 29/06* | (2006.01) |
| *G01N 29/50* | (2006.01) |

(52) U.S. Cl.
CPC .............. *G01M 7/00* (2013.01); *G01N 29/043* (2013.01); *G01N 29/069* (2013.01); *G01N 29/12* (2013.01); *G01N 29/46* (2013.01); *G01N 29/50* (2013.01); *G01N 2291/0258* (2013.01); *G01N 2291/0425* (2013.01); *G01N 2291/0427* (2013.01); *G01N 2291/102* (2013.01); *G01N 2291/2636* (2013.01)

(58) Field of Classification Search
CPC ................... G01N 29/043; G01N 2291/2636
USPC .................................................. 73/623, 602
See application file for complete search history.

(56) References Cited

U.S. PATENT DOCUMENTS

| | | | |
|---|---|---|---|
| 4,092,868 A * | 6/1978 | Thompson et al. | ............. 73/638 |
| 5,619,423 A * | 4/1997 | Scrantz | ............... 73/638 |
| 7,823,454 B2 | 11/2010 | MacLaughlan | |
| 2009/0158850 A1 | 6/2009 | Alleyne et al. | |
| 2009/0217763 A1 | 9/2009 | Yamano | |
| 2010/0071470 A1 | 3/2010 | Junker et al. | |
| 2011/0067497 A1 * | 3/2011 | Grubb et al. | ............... 73/623 |

OTHER PUBLICATIONS

International Preliminary Report on Patentability for PCT/US2012/069613 dated Jun. 24, 2014 (Forms PCT/IB/326, PCT/IB/373, PCT/ISA/237).

* cited by examiner

*Primary Examiner* — John Chapman, Jr.
(74) *Attorney, Agent, or Firm* — Richard J. Coldren; Westinghouse Electric Company LLC

(57) ABSTRACT

The invention relates to systems and methods for conducting an ultrasonic, nondestructive evaluation and inspection of a pipe using Lamb-type wave transducers to detect the presence of defects, flaws, discontinuities and the like. The transducers are positioned within the interior space of the pipe. Two transducers are positioned facing each other such that the ultrasonic beam emitted from each of the transducers is directed toward the other transducer and the portion of pipe to be inspected. The coverage of the transducers is verified and the results are processed using a combination of a cross correlation filter and a signal processing tool.

7 Claims, 1 Drawing Sheet

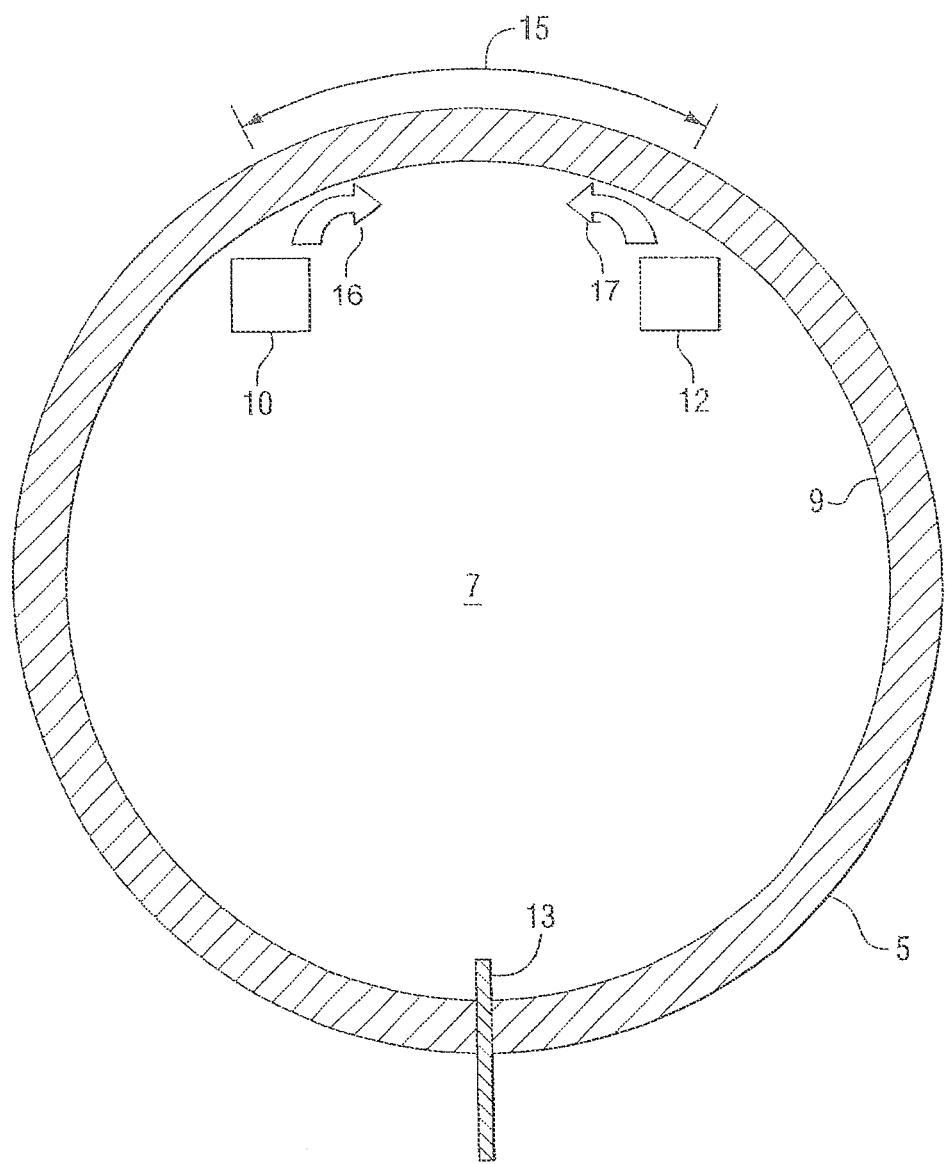

SIGNAL PROCESSING OF LAMB WAVE DATA FOR PIPE INSPECTION

CROSS-REFERENCE TO RELATED APPLICATIONS

This patent application claims the benefit of U.S. Provisional Patent Application Ser. No. 61/570,472 filed on Dec. 14, 2011, and entitled "Signal Processing of Lamb Wave Data for Pipe Inspection".

BACKGROUND

1. Field

This invention pertains to ultrasonic, non-destructive evaluation and testing, and more particularly, to systems and methods for the inspection of piping for the presence of defects, flaws and discontinuities, using Lamb-type wave transducers.

2. Description of Related Art

Non-destructive evaluation (NDE) methods, such as ultrasonic testing (UT), are known in the art and are typically employed to inspect a structure for defects. In general, high frequency sound waves are applied to the structure being tested using one or more transducers. The transducers typically comprise piezocrystal elements that are excited by an electrical voltage in order to induce the ultrasonic waves in the structure. When the sound waves interact with something (e.g., a void; a crack or other defect) having a significant difference in impedance from that of the propagation medium, a portion of the sound is either reflected or diffracted back to the source from which it originated. Detection and quantification of the returned sound pattern is used to determine the characteristics of the reflecting medium. The results obtained from the inspection are utilized to assess the condition and integrity of the structure. Assessment of the structure is based on the characteristics of the detected defects, such as, for example, the size, orientation and location of the defects. The more precise and accurate the inspection technique and data obtained therefrom, the more reliable is the assessment for determining the condition of the structure. It is desired to identify defects to preclude progression to a point where there is a risk to the integrity of the structure and potential structure failure. The consequences of a sudden failure of a structure in a system, such as, for example, an electrical power generation plant, could result in a severe situation.

Ultrasonic technology can provide for computer-controlled excitation (e.g., amplitude and delay) of a probe. The excitation of piezocomposite elements can generate a focused ultrasonic beam with the potential to modify beam parameters such as angle, focal distance, and focal point, through software. Thus, a computer-controlled beam scanning pattern can be implemented in order to "steer" (e.g., direct) the beam to the area of interest and to search for cracks or other discontinuities.

Piping designs and configurations can differ significantly in various systems, such as but not limited to the field of electrical power generation. Some piping systems consist of complex geometries having a plurality of curves, contours, and otherwise irregular geometries. Inspection of the piping using ultrasonic testing techniques is more difficult as the complexity of the geometry of the object to be tested increases. For instance, compound curves make ultrasonic testing very difficult because one portion of the compound curve may, for example, be convex and therefore function to diverge the ultrasonic wave being projected by the transducer while another portion may be, for example, concave and therefore, tend to converge the beam. As a result of the complexity of the design, commercially available ultrasonic inspection has been limited.

The nondestructive evaluation techniques known in the art typically use conventional guided waves which propagate for relatively long distances and therefore, allow for the inspection of a large volume from a single location. However, these conventional guided waves do not provide for the ability to detect smaller sized defects or defects in a difficult to reach area. Furthermore, the nondestructive evaluation techniques known in the art can be time consuming, difficult to implement and provide less than satisfactory results.

Thus, there is a need in the art to design and develop pipe inspection systems and methods that can be performed relatively quickly, are easily implemented and can provide accurate and detailed results which identify even small defects in piping systems having complex geometries. Further, there is a need to employ transducers other than the conventional guided waves used in known ultrasonic testing which can be limiting as to the size of defect which can be detected.

SUMMARY

In one aspect, this invention provides an ultrasonic, non-destructive evaluation system to inspect a pipe for the presence of a defect. The ultrasonic, nondestructive evaluation system includes a first transducer and a second transducer. The first and second transducers are Lamb-type wave transducers which are structured to be positioned within the interior of the pipe. The first transducer is positioned at a first location to emit an ultrasonic beam in a clockwise direction from the first location toward the portion of the pipe which is to be examined and toward the second transducer, and a second transducer is positioned at a second location to emit an ultrasonic beam in a counter-clockwise direction from the second location toward the portion of the pipe which is to be examiner and toward the first transducer. The first and second transducers are spaced a distance apart from each other. The distance is at least twice the distance of a dead zone. The dead zone is a region close to each of the transducers wherein valid frequency data essentially is not obtainable. The system also includes a verification component to confirm the distance that the sound from the first and second transducers is propagated in the pipe. Further, the system includes a data processing component which includes a cross correlation filter and a signal processing tool.

In certain embodiments, the ultrasonic, nondestructive evaluation system can include a control component adapted to control the emission of the ultrasonic beam from the first and second transducers, and to steer and focus the ultrasonic beam to conduct the non-destructive evaluation of the portion of the pipe to be examined. The control system can include a computer and a controller wherein the computer is structured to program the controller which is adapted to manipulate the first and second transducers to perform the non-destructive evaluation.

The first and second transducers can be mounted on a sled assembly to allow the first and second transducers to move in an axial direction and emit the ultrasonic beam in a circumferential direction.

The signal processing tool can include a Synthetic Aperture Focusing Technique.

In another aspect, this invention provides a method for inspecting a pipe to detect the presence of a defect. The method includes positioning a first transducer and a second transducer within the interior of the pipe. The first and second transducers are Lamb-type wave transducers. The first transducer being positioned at a first location to emit an ultrasonic beam in a clockwise direction from the first location toward a portion of the pipe which is to be examined and toward the second transducer, and a second transducer being positioned at a second location to emit an ultrasonic beam in a counter clockwise direction from the second location toward the portion of the pipe which is to be examined and toward the first transducer. The first and second transducers being spaced a distance apart from each other. The distance is at least twice the distance of a dead zone. The dead zone is a region close to each of the transducers wherein valid frequency data essentially is not obtainable. The method further includes a verifying step for confirming the distance that the sound from the first and second transducers is propagated in the pipe. Further, the method includes a data processing step which includes implementing a cross correlation filter and a signal processing tool to enhance the data obtained.

In certain embodiments, the method can include a controlling step for controlling the emission of the ultrasonic beam from the first and second transducers, and for steering and focusing the ultrasonic beam for conducting the non-destructive evaluation of the portion of the pipe being examined. The controlling step can include a computer and a controller wherein the computer is structured for programming the controller which is adapted for manipulating the first and second transducers for performing the non-destructive evaluation.

The method can further include collecting the data and analyzing the data to identify and assess the defect.

The signal processing tool can include a Synthetic Aperture Focusing Technique.

BRIEF DESCRIPTION OF THE DRAWINGS

A further understanding of the invention can be gained from the following description of the preferred embodiments when read in conjunction with the accompanying drawings in which:

FIG. 1 shows a schematic of an ultrasonic inspecting and testing system using Lamb-type wave transducers, in accordance with certain embodiments of the invention.

DESCRIPTION OF THE PREFERRED EMBODIMENT

The invention relates to ultrasonic, nondestructive evaluation and testing systems and methods for inspecting a pipe for the presence of defects, flaws, discontinuities and the like.

Directional phrases used herein relate to the orientation of the elements shown in the drawings and are not limiting upon the claims unless expressly recited.

As employed herein, the phrase "complex geometry" refers to an object that has a variety of different shapes and configurations, such that one portion of the object has a shape or configuration which is substantially different from another portion of the object. For example, without limitation, a compound curve is a complex geometry as used herein. A compound curve is one that changes or varies in more than one direction or dimension (e.g., includes both convex and concave portions).

The inspection systems and methods of the invention are applicable to a wide variety of piping systems. In certain embodiments, the systems and methods of the present invention relate to use with piping systems in an electrical power generation plant, such as but not limited to a pressurized water reactor or a boiling water reactor. It is known in the art to routinely inspect piping systems in an electrical power generation plant for defects, flaws and discontinuities to preclude a potential pipe failure. In particular, piping systems which are subjected to high operational forces and located in corrosive environments can experience stress corrosion cracking which can lead to pipe failure.

The invention utilizes Lamb-type wave transducers to perform a volumetric inspection from the interior, e.g., inside diameter, of the pipe. Like conventional guided waves, Lamb-type waves can propagate for relatively long distances and therefore, allow for the inspection of a large volume from a single location. However, unlike conventional guided waves, Lamb-type waves utilize a spot excitation which allows for insonification of a relatively small cross sectional area. The threshold of detection for any guided waves is typically a five percent change in the cross sectional area and thus, use of the Lamb-type waves results in the ability to detect smaller sized defects or flaws than is obtainable with known systems and methods using conventional guided waves.

In the invention, Lamb-type wave transducers are positioned inside a pipe to be inspected. Suitable Lamb-type wave transducers for use in the invention include those that are known in the art and commercially available. Further, suitable transducers are operable to minimize damping of the signal due to the presence of water, coatings, and the like, disposed in or applied on the surface of the pipe which is to be inspected.

A plurality of Lamb-type wave transducers can be employed and positioned inside the pipe. In certain embodiments, two transducers are used. The transducers are operated in pulse-echo mode for the detection of defects, flaws and discontinuities, and in pitch-catch mode to confirm or verify the extent of coverage of the transducers.

In certain embodiments, two Lamb-type wave transducers are positioned in the interior of a pipe to be inspected and each of the transducers is operable to emit a wave frequency signal which is directed to a portion of the pipe to be inspected. The transducers are positioned such that the signal emitted from each of the transducers is directed toward the other transducer, e.g., they are facing one another. One of the transducers emits a signal in a clockwise direction and the other transducer emits a signal in a counter clockwise direction. Further, the transducers are positioned such that they are spaced a distance apart. The distance may vary. In certain embodiments, the distance between the transducers is at least twice the dead zone or greater than twice the dead zone. The term "dead zone" refers to the region which closely surrounds each of the transducers and wherein valid data essentially cannot be obtained. In one embodiment, the distance is only slightly more than twice the dead zone. It is believed that this spacing, e.g., a distance at least or greater than twice the dead zone, allows for full inspection coverage of the inside diameter of the pipe. For example, each of the transducers can be operated in pulse-echo mode and provide coverage for slightly over 180 degrees beyond the end of its dead zone. Thus, full 360 degree coverage is achieved by collecting and reviewing the frequency data obtained from both transducers.

Positioning the transducers in the interior of the pipe can be accomplished using conventional mechanisms that are known in the art for this purpose. In certain embodiments, the transducers can be mounted on a sled-type assembly which is structured to support a plurality of transducers and to move the transducers in an axial direction through the interior of the pipe while the transducers emit a wave signal in a circumferential direction. In other embodiments, the transducers can be mounted to an interior surface of the pipe.

FIG. 1 shows an ultrasonic, non-destructive evaluation system 1 in accordance with certain embodiments of the invention for testing a pipe 5 having an interior space 7 and an interior surface 9, as shown in FIG. 1. FIG. 1 includes a first transducer 10 and a second transducer 12 positioned within the interior space 7. The first and second transducers 10,12 are Lamb-type wave transducers. The first and second transducers 10,12 are positioned facing one another such that an ultrasonic beam 16 emitted from the first transducer 10 is directed to the second transducer 12 and to a portion of interest of the interior surface 9 of the pipe 5, and an ultrasonic beam 17 emitted from the second transducer 12 is directed to the first transducer 10 and to a portion of interest of the interior surface 9 of the pipe 5. The ultrasonic beam 16 from the first transducer 10 is emitted in a clockwise direction and the ultrasonic beam 1.7 from the second transducer 12 is emitted in a counter clockwise direction. The first and second transducers 10,12 are spaced apart by a distance 15. In certain embodiments, the distance 15 is equivalent to slightly more than twice the distance of the dead zone for each of the first and second transducers 10,12. For example, if the dead zone for each of the transducers 10,12 is approximately 140 mm, then the distance 15 is equal to approximately 300 mm.

A delivery mechanism. may be employed to automatically position and install. the first and second transducers 10,12 in the interior space 7 of the pipe 9. In general, the delivery mechanism provides a mechanism, normally hydraulic or pneumatic, to properly position the first and second transducers 10,12 within the pipe 9.

In general, the use of any guided wave technique requires verification as to how far the sound has propagated in order to confirm coverage. A wide variety of known verification systems and methods can be employed. In certain embodiments, verification is performed as follows. If there is a long seam weld 13 (as shown in FIG. 1) present in the pipe, and this weld 13 has a crown, there is a likelihood that the crown exceeds the five percent change in the cross sectional area (e.g., the threshold of detection for a guided wave) and therefore, the crown reflects the Lamb-type wave. In this embodiment, the transducers are placed so that the end of their dead zone is offset approximately 180 degrees from the weld 13. In such an arrangement, coverage is verified by the sound detected from the reflection from the weld 13. In the embodiment wherein there is no long seam weld 13 in the pipe, for example, the seam weld is ground smooth, or if the seam weld's crown does not produce a reflection, the two transducers are operated in pitch-catch mode as additional channels of data. If the sound from the transmitting transducer is detected after a full 360 degree transit, plus the transducer separation distance, then this verifies that the pulse-echo data can travel 180 degrees and back.

In certain embodiments, the data generated directly from utilizing Lamb-type wave transducers for pipe inspection may be of a quality and resolution that is useful in assessing defects, flaws and discontinuities in a pipe. In other embodiments, it may be desired to enhance the results for improved readability and assessment. In general, Lamb-type wave propagation is dispersive, such that the particle velocity varies with frequency. Further, several propagation modes are generated simultaneously due to the band width of the pulser of the transducer. Each propagation mode has a unique particle motion distribution through the pipe wall.

A processing mechanism, such as a cross correlation filter, may be employed to enhance pipe inspection results generated by Lamb-type wave transducers. The cross correlation filter is applied to the data using the correct frequency. The correct frequency is based on mathematical modeling and observation of a verification signal. Mathematical models that describe the various propagation mode dispersion curves and particle motion are known in the art. These known models are suitable for use in the invention to analyze the frequency spectrum that is generated and to isolate one, unique propagation mode of interest. The frequency predicted by mathematical modeling is confirmed by observing the verification signal. This signal is at the maximum range being inspected and is at a known distance. The use of a Fast Fourier Transform allows the frequency of this verification signal to be identified. The conventional method of isolating the correct mode is accomplished by using a tone burst generator. There are, however, disadvantages with this method. One disadvantage is that the necessary length of the tone burst significantly reduces the spatial and temporal resolution of the data.

In the invention, the temporal resolution is enhanced by using a short square wave pulse (which produces a wider frequency spectrum) and then isolating the correct mode with the cross correlation filter. In the invention, the spatial resolution limitation is addressed by using a signal processing tool, e.g., Synthetic Aperture Focusing Technique (SAFT), which corrects for the beam spread of the sound wave and acts as a velocity filter to further isolate a specific mode. SAFT, for example, is employed for increasing the accuracy of ultrasonic signals in order to improve the resolution of an ultrasonic image and more accurately size detected flaws. A major shortcoming of SAFT is the inherent assumption that the pulse reflected from a flaw has a spectral content that is independent of the location of the flaw relative to the transducer.

The use of a signal processing tool, e.g., SAFT, in combination with a filtering device allows image of the flaw to be reconstructed with less distortion. The signal processing schemes are applied to synthetic flow signals and then to the real flaw.

In the invention, employing a signal processing tool, e.g., SAFT, in conjunction with cross correlation filtering and Lamb wave techniques provide for enhanced results for inspecting a pipe to detect defects or flaw. The use of the cross correlation combined with SAFT (and the mathematical mode modeling) results in converting incoherent noisy data into crisp, sharp images of defects or flaws in the pipe.

In general, the generation of guided and Lamb-type waves can occur in a variety of different modes. Each mode is characterized by various parameters. In certain embodiments of the invention, the items of interest are the refracted sound angle in the material, the frequency of the sound wave, the groups velocity of the sound wave, and the particle motion vector associated with the sound wave. The desirable mode has sound particle motion with a minimal vertical displacement at the pipe surface. This will minimize attenuation from any material (e.g., coating, water, soil and the like) located on the surface and produce a Lamb-type wave with the maximum propagation distance. The mathematical modeling is used to identify candidate modes that have desirable properties. The frequency of candidate modes is used to select the transducer frequency and bandwidth, such that suitable energy will be generated at the candidate frequencies. Refracted angle information is used to design suitable wedges for mounting of the transducers and ultrasonically coupling them to the surface.

When the equipment is deployed, ultrasonic data is acquired at a user-specified interval as each of the transducers is moved along the internal diameter of the pipe. The radio frequency (RF) ultrasonic wave forms are recorded at each data location. These RF wave forms consist of a superposition of all the modes generated by each of the transducers. Since the refracted angle is fixed, each mode is defined by a unique frequency and group velocity value. Thus, to isolate a single mode requires the isolation of a narrow frequency range and velocity.

In certain embodiments of the invention, the selection of the frequency and velocity values for use is determined as follows. The mathematical modeling predicts specific values, but these values are verified by reviewing the data acquired. The process produces a verification signal that has traveled over 360° around the pipe. If the verification signal is the reflection from a long seam weld, it has traveled over 180° down and back. If the verification signal is the pitch catch wrap-around signal, it has traveled over 360° from one transducer to the other transducer. Since the pipe diameter is known and the transducer separation is known, the distance the wrap-around signal traveled is also known. If the long seam weld signal is used for verification, the average of the time of flight for the signal from the two transducers is equal to half of the circumference plus half of the probe separation. In this way, the group velocity of the verification signal can be calculated by dividing the known distance by the time of flight to the signal. A Fast Fourier Transform (FFT) is performed on the verification signal to identify the frequency of the signal.

SAFT can be used as the signal processing tool to act as a velocity filter and to isolate a specific group velocity. The SAFT algorithm is based on the observed phenomena wherein a reflector in a divergent sound field of a transducer produces a characteristic response as the transducer is moved laterally relative to the reflector. The response forms the shape of a hyperbola. The algorithm applies an appropriate time shift to the off-center RF wave forms and sums them. The result is that, if there is a reflector at a given point in the volume, the signals are in phase and the amplitude of the RF wave forms increases. If there is no reflector, the signals are random and sum towards zero. Since the lateral movement is measured as a distance and the RF signal is measured in time, the sound velocity of the RF wave form must be correct for the appropriate time shift to be applied to stay along the hyperbolic curve. When a given velocity is used with the SAFT algorithm, it will enhance the modes with that velocity and suppress modes with different velocities. Thus, if multiple modes overlap with the verification signal, the SAFT processing can isolate a single group velocity that can be processed with the FFT to identify the frequency. If multiple modes are predicted or observed, this process is repeated as necessary to verify the group velocity and associated frequency for all modes.

In certain embodiments, an identified candidate frequency is input into the cross correlation filter. The number of cycles for the correlated signal is a user input parameter. A typical value for the number of cycles is 2 or 4. The cross correlation filter generates a new RF trace wherein the amplitude corresponds to the percent correlation to the specified frequency. This produces a B-scan image of the cross correlation data.

The SAFT algorithm is then applied, using suitable parameters to isolate the desired group velocity and enhance the spatial resolution. This process is repeated for all candidate modes.

The result is a B-scan presentation of a single mode of Lamb-type wave ultrasonic data that can be analyzed for the presence of reflectors. The location and axial extent of these indications can be determined from this data display.

While specific embodiments of the invention have been described in detail, it will be appreciated by those skilled in the art that various modifications and alternatives to those details could be developed in light of the overall teachings of the disclosure. Accordingly, the particular embodiments disclosed are meant to be illustrative only and not limiting as to the scope of the invention which is to be given the full breadth of the appended claims and any and all equivalents thereof.

What is claimed is:

1. An ultrasonic, nondestructive evaluation system to provide 360-degree inspection coverage for an interior surface of a pipe to detect presence of a defect, comprising:
   a first transducer;
   a second transducer; and
   a means for operating each of the first and second transducers in pulse echo-mode,
   wherein, the first and second transducers are Lamb-type wave transducers and structured to be positioned within an interior space of the pipe, the first and second transducers are spaced a distance apart and facing one another, the first transducer is positioned at a first location to emit a first ultrasonic beam in a clockwise direction from the first location toward a portion of the pipe which is to be examined and toward the second transducer, and the second transducer is positioned at a second location to emit a second ultrasonic beam in a counter-clockwise direction from the second location toward a portion of the pipe which is to be examined and toward the first transducer,
   wherein each of the first and second transducers has a dead zone associated therewith and the distance between the first and second transducers is at least twice the distance of the dead zone, the first transducer provides inspection coverage for 180-degrees or more beyond the dead zone associated therewith and the second transducer provides inspection coverage for 180-degrees or more beyond the dead zone associated therewith, such that the 360-degree inspection coverage is provided by a combination of the first and second transducers.

2. The system of claim 1, further comprising:
   a means for generating a plurality of propagation modes simultaneously; and
   a means for Synthetic Aperture Focusing.

3. The system of claim 1, further comprising:
   a means for operating the first and second transducers in pulse-echo mode for detection of the defect and in pitch-catch mode to verify distance traveled by sound generated by each of the first and second transducers.

4. A method of performing a 360-degree inspection for an interior surface of pipe to detect presence of a defect, comprising:
   introducing a first transducer into an interior of the pipe;
   introducing a second transducer into an interior of the pipe,
   wherein, each of the first and second transducers is a Lamb-type wave transducer and each has associated therewith a dead zone;
   positioning the first transducer at a first location;
   positioning the second transducer at a second location,
   wherein the first and second transducers are spaced a distance apart and are facing each other;
   emitting a first ultrasonic beam in a clockwise direction from the first location toward a portion of the pipe which is to be examined and toward the second transducer;
   emitting a second ultrasonic beam in a counter-clockwise direction from the second location toward a portion of the pipe which is to be examined and toward the first transducer;
   adjusting the distance to at least twice the distance of the dead zone;
   operating each of the first and second transducers in pulse-echo mode;

employing the first transducer to provide inspection for 180-degrees or more beyond the dead zone associated therewith;

employing the second transducer to provide inspection for 180-degrees or more beyond the dead zone associated therewith; and combining data generated by both of the first and second transducers for the 360-degree inspection of the interior surface of the pipe.

5. The method of claim 4, further comprising collecting the data and analyzing the data to identify and assess a flaw in the pipe.

6. The method of claim 4, further comprising:
isolating a specific mode from a plurality of propagation modes generated simultaneously by each of the first and second ultrasonic beams.

7. The method of claim 4, further comprising:
verifying distance traveled by sound generated by the first and second transducers to confirm inspection coverage of the pipe, comprising:
locating a seam weld in the pipe;
placing the first and second transducers such that the dead zone associated with each of the transducers is offset by about 180 degrees from the seam weld; and
detecting the sound being reflected from the seam weld.

* * * * *